United States Patent [19]
Iwanaga et al.

[11] Patent Number: 5,965,725
[45] Date of Patent: Oct. 12, 1999

[54] POLYPEPTIDES, AND PREPARATION AND DNA ENCODING THEREOF

[75] Inventors: Sadaaki Iwanaga; Shun-ichiro Kawabata; Tetsu Saito, all of Fukuoka, Japan

[73] Assignee: Seikagaku Kogyo Kabushiki Kaisha, Japan

[21] Appl. No.: 09/018,170

[22] Filed: Feb. 3, 1998

Related U.S. Application Data

[62] Division of application No. 08/505,617, Jul. 21, 1995, Pat. No. 5,861,378.

[30] Foreign Application Priority Data

Jul. 22, 1994 [JP] Japan .................................. 6-191850
Sep. 1, 1994 [JP] Japan .................................. 6-232025

[51] Int. Cl.$^6$ .......................... C07H 21/04; A61K 38/00
[52] U.S. Cl. .......................................... 536/23.5; 530/324
[58] Field of Search ............................ 530/324; 536/23.5

[56] References Cited

U.S. PATENT DOCUMENTS 5,242,902  9/1993  Murphy et al. ........................... 514/12

Primary Examiner—Robert A. Wax
Assistant Examiner—Einar Stole
Attorney, Agent, or Firm—Testa, Hurwitz & Thibeault, LLP

[57] ABSTRACT

The present invention relates to polypeptide having a primary structure of amino acid sequence shown by Sequence List Sequence No. 1 and DNA encoding for the polypeptide. The polypeptide is obtainable by following steps (1)–(3):

Step (1): extracting small granule fraction of homocytes of horseshoe crab with a buffer containing protein denaturing agent and chelating agent, Step (2): subjecting said extract to reverse phase high performance liquid chromatography, Step (3): eluting by concentration gradient elution with a hydrophobic organic solvent.

Also, the polypeptide is produced by chemical synthesis. The polypeptide has similar chemical structure to defensin and is useful as gargles, disinfectants, antiseptics or antimicrobials.

3 Claims, 1 Drawing Sheet

POLYPEPTIDES, AND PREPARATION AND DNA ENCODING THEREOF

This is a divisional application of U.S. application Ser. No. 08/505,617, filed on Jul. 21, 1995 now U.S. Pat. No. 5,861,378.

FIELD OF THE INVENTION

This invention relates to polypeptides having antimicrobial activities against bacteria including Gram positive and negative bacteria, and fungi, and preparation thereof and DNA encoding for said polypeptides.

The polypeptides of the present invention possesses potent antimicrobial activity, thus are useful as antimicrobial, bactericidal and antiseptic agents against various microorganisms.

BACKGROUND OF THE INVENTION

Horseshoe crab has a type of hemocytes in the body and the hemocytes are filled with two kinds of large and small granules having different densities. The large granules contain a body fluid coagulation factor and an anti-lipopolysaccharide factor, and the small granules contain antimicrobial substances such as tachyplesin. The inventors of the present invention isolated six proteins, S1–S6, from hemocytes of horseshoe crab as components of small granules (Shigenaga, T. et al., J. Biochem., 114, 307–316 (1993)).

In addition, a group of peptides having antimicrobial activity and generally called defensins were isolated from cellular granules of neutrophils and macrophages of mammals such as human being, rabbits, guinea pigs and rats, and their total amino acid sequences are disclosed in U.S. Pat. No. 5,242,902. The growth stimulant effect on epidermal cells and fibroblast cells of defensins were disclosed in said U.S. Pat. No. 5,242,902 in addition to the antimicrobial activity against Gram negative and positive bacteria and fungi. Defensins are basic peptides having about 30 amino acid residues with common components of six cysteine residues and three disulfide bonds.

No polypeptide isolated from the hemocytes of horseshoe crab having similar amino acid sequence with those of defensins has been reported. Furthermore, no nucleotide sequence corresponding to the amino acid sequence of polypeptide of the present invention has been known.

The inventors of the present invention further investigated the S5 peptide fraction in the isolated components of small granule fractions of hemocytes of horseshoe crab and determined its total amino acid sequence. The amino acid sequence has a similar structure in the C-terminal with that of known defensins. The antimicrobial activity of S5 peptide fraction was further investigated and S5 peptide fraction was found to have potent antimicrobial activities against Gram positive and negative bacteria and fungi, and accomplished the present invention.

SUMMARY OF THE INVENTION

One object of the present invention is to provide a DNA encoding for polypeptides which show strong physiological activity against Gram positive and negative bacteria and fungi.

The other object of the present invention is to provide polypeptides at least having a primary structure of amino acid sequence shown by the following [Formula 1] (SEQ ID NO:7).

```
AA1 AA2 Cys AA2 AA2 AA2 AA1 AA2 AA4 Cys Arg Ser AA1 Cys Phe      [Formula 1] (SEQ ID NO:7)
             5                  10                      15

Arg AA1 Glu AA4 AA2 AA3 AA2 AA4 AA4 Ser Ala AA2 Cys Gly Arg
             20                  25                      30

Tyr AA4 Cys Cys Arg AA2 AA1
             35
```

(wherein, AA1 represents a basic amino acid residue, AA2 represents a neutral amino acid residue, AA3 represents an acidic amino acid residue AA4 represents an aromatic amino acid residue, respectively. The cysteine residues at 3rd, 10th, 14th, 28th, 33rd and 34th positions may form disulfide bond (—S—S—) between at least one combination of 3rd and 34th, 10th and 28th, and 14th and 33rd positions.)

Another object of the present invention is to provide a polypeptide comprising a primary structure of amino acid sequence shown by the following [Formula 3] (SEQ ID NO:1).

```
Asn Pro Leu Ile Pro Ala Ile Tyr Ile Gly Ala Thr Val Gly Pro      [Formula 3(SEQ ID NO:1)]
 1               5                  10                      15

Ser Val Trp Ala Tyr Leu Val Ala Leu Val Gly Ala Ala Ala Val
                  20                  25                      30

Thr Ala Ala Asn Ile Arg Arg Ala Ser Ser Asp Asn His Ser Cys
                  35                  40                      45

Ala Gly Asn Arg Gly Trp Cys Arg Ser Lys Cys Phe Arg His Glu
                  50                  55                      60

Tyr Val Asp Thr Tyr Tyr Ser Ala Val Cys Gly Arg Tyr Phe Cys
                  65                  70                      75

Cys Arg Ser Arg
```

(wherein, cysteine residues at 45th, 52nd, 56th, 70th, 75th and 76th positions may form disulfide bond (—S—S—) between at least one combination of 45th and 76th, 52nd and 70th, and 56th and 75th positions.)

Another further object of the present invention is to provide an antimicrobial polypeptide comprising a fraction obtained by extracting small granule fraction of hemocytes of horseshoe crab with a buffer containing guanidine and chelating agent, subjecting the extract to reverse phase high performance liquid chromatography, and eluting by concentration gradient elution with acetonitrile, said polypeptide having the following physicochemical properties:

(i) a single band by SDS-PAGE under reducing condition;
(ii) a molecular weight of about 8,200 as estimated by SDS-PAGE under reducing condition;
(iii) comprises 79 amino acids; and
(iv) antimicrobial activities against Gram negative and positive bacteria, and fungi.

A further object of the present invention is to provide a process for producing a polypeptide comprising the primary structure of amino acid sequence shown by above mentioned [Formula 1] (SEQ ID NO:7), which process comprises extracting small granule fraction of hemocytes of horseshoe crab with a buffer containing protein denaturing agent and chelating agent, subjecting the extract to reverse phase high performance liquid chromatography, and eluting with a hydrophobic organic solvent.

The other further object of the present invention is to provide a single stranded DNA comprising a nucleotide sequence encoding for the polypeptide shown by above mentioned [Formula 3] (SEQ ID NO:4), or a double stranded DNA composed of said DNA and a complementary DNA.

A further object of the present invention is to provide a polypeptide comprising a primary structure of amino acid sequence shown by [Formula 4] (SEQ ID NO:3).

```
Ala Ser Ser Asp Asn His Ser Cys Ala Gly Asn Arg Gly Trp Cys    [Formula 4] (SEQ ID NO:3)
 1           5                  10                      15
Arg Ser Lys Cys Phe Arg His Glu Tyr Val Asp Thr Tyr Tyr Ser
            20                  25                      30
Ala Val Cys Gly Arg Tyr Phe Cys Cys Arg Ser Arg
            35                  40
```

(wherein, one Arg may be bound through peptide linkage to amino terminal and cysteine residues at 8th, 15th, 19th, 33rd, 38th and 39th positions may form disulfide bond (—S—S—) between at least one combination of 8th and 39th, 15th and 33rd, and 19th and 38th positions).

A further object of the present invention is to provide a polypeptide comprising a primary structure of amino acid sequence shown by [Formula 5] (SEQ ID NO:4).

```
Asn Pro Leu Ile Pro Ala Ile Tyr Ile Gly Ala Thr Val Gly Pro    [Formula 5] (SEQ ID NO:4)
 1           5                  10                      15
Ser Val Trp Ala Tyr Leu Val Ala Leu Val Gly Ala Ala Val
            20                  25                      30
Thr Ala Ala Asn Ile Arg
            35
```

(wherein, one Arg may be bound through peptide linkage to the carboxyl terminal.)

Further objects of the present invention will be clearly shown by the following disclosure.

DETAILED DESCRIPTION OF THE INVENTION AND PREFERRED EMBODIMENT

Figure 1:
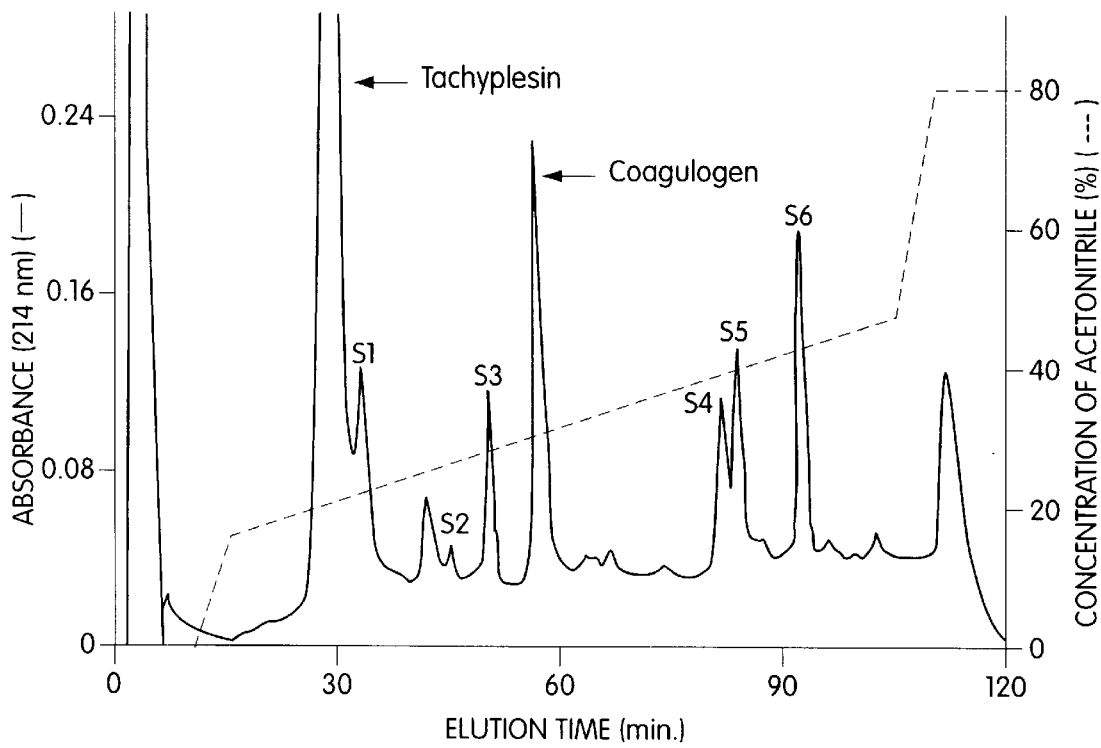
FIG. 1 shows an elution curve of the polypeptide of the present invention from TSK gel Phenyl 5PW-RP column by concentration gradient elution with acetonitrile method described by Example 1.

That is, this invention provides polypeptides shown by following 1)–6).

1) A polypeptide at least having a primary structure of amino acid sequence shown by the following [Formula 1] (SEQ ID NO:7).

```
AA1 AA2 Cys AA2 AA2 AA2 AA1 AA2 AA4 Cys Arg Ser AA1 Cys Phe    [Formula 1] (SEQ ID NO:7)
            5                   10                  15

Arg AA1 Glu AA4 AA2 AA3 AA2 AA4 AA4 Ser Ala AA2 Cys Gly Arg
                20              25                  30

Tyr AA4 Cys Cys Arg AA2 AA1
                35
```

(wherein, AA1 represents a basic amino acid residue, AA2 represents a neutral amino acid residue, AA3 represents an acidic amino acid residue, and AA4 represents an aromatic amino acid residue respectively. The cysteine residues at 3rd, 10th, 14th, 28th, 33rd and 34th positions may form disulfide bond (—S—S—) between at least one combination of 3rd and 34th, 10th and 28th, and 14th and 33rd positions.)

2) The polypeptide according to the above mentioned 1), wherein AA1 represents a basic L-amino acid residue selected from the group composed of Arg, Lys and His, AA2 represents a neutral L-amino acid residue selected from the group composed of Gly, Ala, Leu, Val, Ile, Met, Pro, Asn, Thr, Ser and Gln, AA3 represents an acidic L-amino acid residue selected from the group composed of Asp and Glu, and AA4 represents an aromatic L-amino acid residue selected from the group composed of Trp, Tyr and Phe in [Formula 1] (SEQ ID NO:7).

3) A polypeptide at least having a primary structure of amino acid sequence shown by the following [Formula 2] (SEQ ID NO:2).

```
His Ser Cys Ala Gly Asn Arg Gly Trp Cys Arg Ser Lys Cys Phe    [Formula 2] (SEQ ID NO:2)
            5                   10                  15

Arg His Glu Tyr Val Asp Thr Tyr Tyr Ser Ala Val Cys Gly Arg
                20              25                  30

Tyr Phe Cys Cys Arg Ser Arg
                35
```

(wherein cysteine residues at 3rd, 10th, 14th, 28th, 33rd and 34th positions may form disulfide bond (—S—S—) between at least one combination of 3rd and 34th, 10th and 28th, and 14th and 33rd positions.)

4) The antimicrobial polypeptide comprising a primary structure shown by [Formula 2] (SEQ ID NO:2) of above 3) at a carboxyl terminal and a hydrophobic polypeptide region at an amino terminal.

5) A polypeptide comprising a primary structure of amino acid sequence shown by [Formula 3] (SEQ ID NO:1).

(wherein cysteine residues at 45th, 52nd, 56th, 70th, 75th and 76th positions may form disulfide bond (—S—S—) between at least one combination of 45th and 76th, 52nd and 70th, and 56th and 75th positions.).

6) An antimicrobial polypeptide comprising a fraction obtained by extracting small granule fraction of hemocytes of horseshoe crab with a buffer containing guanidine and chelating agent, subjecting the extract to reverse phase high performance liquid chromatography, and eluting by concentration gradient elution with acetonitrile, showing the following physicochemical properties:

(i) a single band by SDS-PAGE under reducing condition;
(ii) a molecular weight of about 8,200 as estimated by SDS-PAGE under reducing condition;
(iii) comprises 79 amino acids; and
(iv) antimicrobial activities against Gram negative and positive bacteria, and fungi.

This invention further provides polypeptides obtained by digestion of the polypeptide shown by [Formula 3] (SEQ ID NO:1) of above 5) with a protease.

Further, this invention provides a polypeptide comprising a primary structure of amino acid sequence shown by [Formula 4] (SEQ ID NO:3), and a polypeptide comprising a primary structure of amino acid sequence shown by [Formula 5] (SEQ ID NO:4),

```
Asn Pro Leu Ile Pro Ala Ile Tyr Ile Gly Ala Thr Val Gly Pro   [Formula 3(SEQ ID NO:1)]
 1           5                   10                  15

Ser Val Trp Ala Tyr Leu Val Ala Leu Val Gly Ala Ala Ala Val
                20              25                  30

Thr Ala Ala Asn Ile Arg Arg Ala Ser Ser Asp Asn His Ser Cys
                35              40                  45

Ala Gly Asn Arg Gly Trp Cys Arg Ser Lys Cys Phe Arg His Glu
                50              55                  60

Tyr Val Asp Thr Tyr Tyr Ser Ala Val Cys Gly Arg Tyr Phe Cys
                65              70                  75

Cys Arg Ser Arg
```

```
Ala Ser Ser Asp Asn His Ser Cys Ala Gly Asn Arg Gly Trp Cys    [Formula 4] (SEQ ID NO:3)
 1           5               10                  15

Arg Ser Lys Cys Phe Arg His Glu Tyr Val Asp Thr Tyr Tyr Ser
            20              25              30

Ala Val Cys Gly Arg Tyr Phe Cys Cys Arg Ser Arg
                35              40
```

(wherein, one Arg may be bound through peptide linkage to the amino terminal and cysteine residues at 8th, 15th, 19th, 33rd, 38th and 39th positions may form disulfide bond (—S—S—) between at least one combination of 8th and 39th, 15th and 33rd, and 19th and 38th positions.)

```
Asn Pro Leu Ile Pro Ala Ile Tyr Ile Gly Ala Thr Val Gly Pro    [Formula 5] (SEQ ID NO:4)
 1           5              10                   15

Ser Val Trp Ala Tyr Leu Val Ala Leu Val Gly Ala Ala Ala Val
            20              25              30

Thr Ala Ala Asn Ile Arg
                35
```

(wherein, one Arg may be bound through peptide linkage to the carboxyl terminal.)

In addition, the present invention provides antimicrobial agents comprising these polypeptides or pharmacologically acceptable salts thereof as effective ingredient.

Further, the present invention provides a single stranded DNA comprising a nucleotide sequence encoding for the polypeptide shown by [Formula 3] (SEQ ID NO:4) above 5) or a double stranded DNA composed of said DNA and a complementary DNA.

Furthermore, the present invention provides a process for producing a polypeptide according to one of the polypeptides disclosed in above 1)–6), which process comprises extracting small granule fraction of hemocytes of horseshoe crab with a buffer containing protein denaturing agent and chelating agent, subjecting the extract to reverse phase high performance liquid chromatography, and eluting with a hydrophobic organic solvent.

The raw material small granule fraction of hemocytes of horseshoe crab used for the present invention includes small granule fraction of hemocytes obtained from the blood of horseshoe crabs, for example, *Limulus polyphemus, Tachypleus tridentatus, Tachypleus gigas* and *Carcinoscorpius rotundicauda*.

Hemocytes are separated from the blood of horseshoe crab, and small granules are separated from said hemocytes to give the desired small granule fraction.

Practically, for example, isolated hemocytes of horseshoe crab are suspended in 0.008M Tris-HCl buffer containing 0.001M propranolol, 0.001M phenylmethanesulfonyl fluoride (PMSF) and 0.75M sucrose, pH 7.4. The suspension is shaken for a while, centrifuged to give a supernatant. The supernatant is mixed with heparin to give final concentration of 40 USP unit/ml, centrifuged to give an upper layer. The upper layer is centrifuged using 1.5–2.4M sucrose density gradient solution containing 0.008M Tris-HCl buffer (pH 7.4), 0.001M PMSF and heparin (40 USP unit/ml) at 112,000×g for 30 min. The separated lower layer is collected and used as the small granule fraction.

The obtained sniall granule fraction of hemocytes of horseshoe crab is ① sonicated in a suitable buffer such as 0.02M Tris-HCl buffer containing 6M guanidine and 0.002M ethylenediaminetetraacetic acid (EDTA), pH 8.0, and extracted after the incubation at 37° C. for one hr., ② the extract is subjected to reverse phase HPLC using TSK gel Phenyl 5PW-RP (TOSOH Corp.) as a carrier and concentration-gradiently eluted with acetonitrile to give the S5 fraction of antimicrobial polypeptide of the present invention.

The eluted fraction, S5, obtained by the reverse phase HPLC in step ② may be further purified by reverse phase HPLC using TSK gel ODS120T (TOSOH Corp.) as a carrier. The determination of peptide content during the purification process can be carried out by measuring the ultraviolet absorption at a wave length of 214 nm.

The polypeptides of the present invention can be prepared by processes known per se, for example, solution or solid phase syntheses (Nobuo Izumiya, Tetsuo Kato, Haruhiko Aoyagi and Michinori Waki, "Fundamentals and Experiments of Peptide Synthesis", 1985, Pub. by Maruzen Co., Ltd.). For example, preparation of the straight chain polypeptide of [Formula 1] (SEQ ID NO:7) having Arg residue at 37th position in the amino acid sequence by a solid phase synthetic method is carried out by direct or indirect coupling via a spacer of the carboxyl group of N-protected arginine to an insoluble resin having chloromethyl or hydroxymethyl group, then stepwisely coupling 36th to 1st protected amino acids in the amino acid sequence order by the solid phase synthetic method, and eliminating the insoluble resin and the protecting group to give the straight chain polypeptide of [Formula 1] (SEQ ID NO:7). Further, the three pairs of cysteine residues at 3rd and 34th, 10th and 28th, and 14th and 33rd of the obtained polypeptide may form the respective disulfide bond independently through their mercapto groups.

These disulfide bonds may be formed by methods known per se, for example by mild air oxidation.

The insoluble resin having said chloromethyl or hydroxymethyl group and spacer used for the synthesis of polypeptides of the present invention, in some cases N-protected amino acid resins prepared by coupling N-protected amino acid with said insoluble resin can be prepared by known methods and various types of said insoluble resin, said spacer, and said N-protected amino acid coupled insoluble resins are commercially available.

Any insoluble resins which can directly or occasionally via a spacer couples with carboxyl group of C-terminal N-protected amino acid, and then are removable from the carboxyl group can be used for the present invention. These insoluble resins, for example, chloromethyl resin (chloromethylated styrene-divinylbenzene copolymer), hydroxymethyl resin or 4-hydroxymethyl-Pam (phenylacetamidomethyl)-resin with spacer for Boc (t-butyloxycarbonyl) strategy, and hydroxymethylphenoxymethyl resin (Wang) resin and their derivatives for Fmoc (9-fluorenylmethyloxycarbonyl) strategy are preferably used.

The protected amino acids are amino acids having protected functional group with a protecting group by known methods, and various protected amino acids are commercially available. For the synthesis of polypeptides of the present invention, the below mentioned protecting groups are preferably selected. The protecting groups of α-amino group of amino acid include Boc (t-butyloxycarbonyl) and Fmoc (9-fluorenylmethyloxycarbonyl) groups. The protecting groups of guanidino group of arginine (Arg) include Tos (tosyl), $NO_2$ (nitro), Mtr (4-methoxy-2,3,6-trimethylbenzene-sulfonyl), and Pmc (2,2,5,7,8-pentamethylchroman-6-sulfonyl) groups. The protecting groups of ε-amino group of lysine (Lys) include Z (benzyloxycarbonyl), Cl.Z (2-chlorobenzyloxycarbonyl), Boc, Npys (3-nitro-2-pyridinesulfenyl) groups. The protecting groups of imidazolyl group of histidine (His) include Tos, Z, Pac (phenacyl), Bom (benzyloxymethyl), Dnp (dinitrophenyl) and Trt (trityl) groups. The protecting groups of mercapto group of cysteine (Cys) include Bzl (benzyl), MBzl (4methoxybenzyl), 4-MeBzl (4-methylbenzyl), Acm (acetamidomethyl), Trt, Npys, t-Bu (t-butyl) and t-BuS (t-butylthio) groups, and MBzl, 4-MeBzl, Trt, Acm and Npys groups are preferably used. The protecting groups of hydroxy groups of tyrosine (Tyr) include Bzl, C12.Bzl (2,6-dichlorobenzyl) and t-Bu groups, but tyrosine may be used without protection. The protecting group of indole group of tryptophan (Trp) includes CHO (formyl) group but tryptophan may be used without protection. The protecting group of thiomethyl group of methionine (Met) includes methylsulfoxide group but methionine may be used without protection. The protecting groups of hydroxy group of serine (Ser) and threonine (Thr) include Bzl and t-Bu groups. The protecting groups of carboxyl group of aspartic acid (Asp) and glutamic acid (Glu) include OBzl (benzyl ester), OtBu (t-butyl ester), OcHex (cyclohexyl ester) and OPac (phenacyl ester) groups. The protecting groups of carbamide group of asparagine (Asn) and glutamine (Gln) include Trt and Xan (xanthyl) groups.

Each protecting group is suitably selected from known protecting groups according to the reaction conditions for peptide synthesis.

The coupling of the protected amino acids is carried out by conventional condensation methods, for example, methods of DCC (dicyclohexylcarbodiimide), DIPCDI (diisopropyl-carbodiimide) [Tartar, A., et al.; J. Org. Chem., 44, 5000 (1979)], active ester, mixed or symmetric acid anhydride, carbonyldiimidazole, DCC-HOBt (1-hydroxybenzotriazole) [Keonig, W., et al.; Chem. Ber., 103, 788, 2024, 2034 (1970)], diphenyl phosphoryl azide, BOP-HOBt using BOP reagent (benzotriazolyl-N-hydroxy tris(dimethylamino)phosphonium hexafluorophosphate) (Hudson, D., J. Org. Chem., 53, 617 (1988)), HBTU (2-(1H)-benzotriazol-1-yl)-1,1,3,3-tetramethyluronium hexafluorophosphate)-HOBt (Knorr, R., et al., Tetrahedron Lett., 30, 1927 (1989)) and TBTU (2-(1H)-benzotriazol-1-yl)-1,1,3,3-tetramethyluronium tetrafluoroborate)-HOBt (Knorr, R., et al. Tetrahedron Lett., 30, 1927 (1989)). However, methods of DCC, DCC-HOBt, BOP-HOBt, HBTU-HOBt and symmetric acid anhydride are preferably used.

These condensation reactions are generally carried out in an organic solvent such as dichloromethane, dimethylformamide (DMF) and N-methylpyrrolidone (NMP) or mixtures thereof.

The eliminating reagents of the protecting group of α-amino group include such as trifluoroacetic acid/dichloromethane, HCl/dioxane, piperidine/DMF and piperidine/NMP, and are suitably selected according to the properties of the protecting group to be eliminated.

The degree of progress of the condensation reaction in the respective synthetic steps is examined and monitored by the method of Kaiser, E., et al. (ninhydrin reaction method) [Anal. Biochem., 34, 595 (1970)].

The protected peptide resins having the desired amino acid sequences can be obtained by the methods shown above.

The protected peptide resins are treated with HF, TFMSA (trifluoromethanesulfonic acid) (Yajima, H., et al.; "The Peptides" 5, 65 (1983), ed. by Gross, E., pub. by Academic Press), TMSOTf (trimethylsilyl triflate) [Fujii,N., et al.; J. Chem. Soc., Chem. Commun., 274 (1987)], TMSBr (trimethylsilyl bromide) [Fujii, N., et al., Chem. Pharma. Bull., 35, 3880 (1987)] or trifluoroacetic acid (TFA) to simultaneously eliminate said resins and protecting groups. The above mentioned eliminating reagents are suitably selected according to the said strategy (Boc or Fmoc), resins and protecting groups, respectively.

Then, the resultant peptides can be reduced with a reducing agent such as 2-mercaptoethanol and DTT (dithiothreitol) to secure reduced form of mercapto group of the cysteine, and the mercapto groups are oxidized to give cyclic peptides with disulfide (—S—S—) bond.

The oxidizing treatment can be performed by methods known per se and generally oxygen in the air or an oxidizing agent such as ferricyanate (for example potassium ferricyanate) is used.

The resultant polypeptides are isolated and purified by known methods in the field of peptide chemistry, for example, extraction, re-crystallization, various chromatography (such as gel filtration, ion exchange, partition, absorption and reversed phase chromatography), electrophoresis, and counter current distribution. Among them, reversed phase high performance liquid chromatography (HPLC) is most effective.

The symbols used for the amino acid residues of polypeptides in the specification of the present invention are expressed by the internationally authorized three letter symbols. That is, each symbol represents the below mentioned amino acid residue, respectively.

His; histidine, Ser; serine, Cys; cysteine,
Ala; alanine, Gly; glycine, Asn; asparagine,
Arg; arginine, Trp; tryptophan, Lys; lysine,
Phe; phenylalanine, Glu; glutamic acid, Tyr; tyrosine,
Val; valine, Asp; aspartic acid, Thr; threonine,
Leu; leucine, Ile; isoleucine, Met; methionine,
Pro; proline, Gln; Glutamine.

Cysteine residues without formation of disulfide bonds, or those obtained by reduction of disulfide bonds by known methods such as reduction with a reducing agent, e.g. dithiothreitol, may be carboxymethylated with known methods such as reaction with iodoacetic acid to give carboxymethylated polypeptide derivatives of the present invention. These carboxymethylated polypeptide derivatives also exhibit potent antimicrobial activity against Gram negative and positive bacteria.

The fractions of polypeptides of the present invention can be obtained by degradation of the polypeptide shown by above mentioned [Formula 3] (SEQ ID NO:1) of the present invention with conventional methods known per se using a protease such as trypsin, chymotrypsin or pepsin. The resultant polypeptides may be isolated and purified by known methods in the field of peptide chemistry, among them reversed phase HPLC is most effective.

According to the present invention, a DNA (AAT to CGC; nucleotide sequence Nos. 135–371) of SEQ ID NO:5 encoding for a polypeptide shown by amino acid sequence (Asn to Arg; amino acid Nos. 1–79) of SEQ ID NO:1 in [Formula 3] (SEQ ID NO:1) can be obtained. In addition, DNAs encoding for polypeptides of [Formula 2] (SEQ ID NO:2), [Formula 4] (SEQ ID NO:3) and [Formula 5] (SEQ ID NO:4) each having a common amino acid sequence region with that of polypeptide of [Formula 3] (SEQ ID NO:1) can be obtained by the similar method.

That is, an oligonucleotide is synthesized based on the partial amino acid sequences of the polypeptide shown by amino acid sequence of [Formula 3] (SEQ ID NO:1). cDNA encoding for said polypeptide are isolated from cDNA library, which are prepared from poly(A)$^+$ RNA isolated from horseshoe crab hemocytes, using said oligonucleotides or antibodies against polypeptide. Then the nucleotide sequences of these cDNA can be confirmed using dideoxy chain termination method (Sanger, F., et al., Proc. Natl. Acad. Sci., U.S.A. 74, 5463–5467 (1977)) to give DNAs of the present invention. Furthermore, the amino acid sequences of the polypeptides can be determined from the determined nucleotide sequences and above mentioned partial amino acid sequences. In addition, regarding to the nucleotide sequence in the region encoding for the polypeptide, DNAs obtained by substitution with the other nucleotide to give the other codon which corresponds to the same amino acid so as not to form different amino acid sequence are included within the scope of the present invention.

Further, the polypeptides of the present invention can be prepared by the following procedures using DNAs of the present invention.

DNAs encoding for the peptides of the present invention obtained by the above mentioned procedure are cleaved by treatment with ultrasonic or restriction enzyme, or the other methods known to the field of gene technology, and subcloned into a suitable vector. The subcloned vectors is transfected into suitable host organisms or cells to give transformants. The transformants are bred or cultured by suitable conditions to stably produce a large amount of polypeptides. The conditions for breeding and culture of transformants can be suitably selected from the conditions known for the production of polypeptides including well known conditions in the field of gene technology suitable for the growth of hosts used. The aimed polypeptides can be obtained by generally known isolation and purification procedures of proteins in the field of gene technology and protein chemistry.

The polypeptides of the present invention exhibit base characteristics due to characteristic features of their constitutional amino acids and form salts with acids. For example, the polypeptides form salts with inorganic acids e.g. hydrochloric acid, hydrobromic acid, phosphoric acid, nitric acid and sulfuric acid, organic carboxylic acids e.g. acetic acid, propionic acid, maleic acid, succinic acid, malic acid, citric acid, tartaric acid and salicylic acid, acidic sugars e.g. glucuronic acid, galacturonic acid, gluconic acid and ascorbic acid, acidic polysaccharides e.g. hyaluronic acid, chondroitin sulfate and alginic acid, or organic sulfonic acid e.g. methanesulfonic acid and p-toluenesulfonic acid. The polypeptides of the present invention can be used as medicinally acceptable salts thereof.

The polypeptides and salts thereof of the present invention can be used as gargles, disinfectants, antiseptics and antimicrobials in the forms of compositions composed of the said polypeptides and salts thereof as effective ingredient and pharmaceutically acceptable carriers selected according to the methods and forms of administration. That is, gargles, disinfectants, antiseptics and antimicrobials composed of effective ingredient of the polypeptides of the present invention can be used, according to the treatment or disinfection method of infected sites including out side and inside of body, parenterally as external preparations, injection preparations and suppositories, or orally with suitable pharmaceutical carriers according to the methods of administration in the form of preparations such as powder granules, solution for injection or oral administration, tablets, suppositories, pessaries, ointments, creams and aerosols.

When the antimicrobials composed of polypeptides of the present invention as effective ingredients are directly administered as injection preparations to a living body, the polypeptides or salts thereof of the present invention may be dissolved in a saline solution and successively or intermittently administered by drip infusion or intravenous injection.

Furthermore, the polypeptides of the present invention contain amino acid sequence similar to that of defensin, thus, wound healing effect is expected.

The dose of the polypeptides of the present invention vary with the symptoms, genders and ages of patients, and route of administration. The parenteral daily dose for adult patient is 0.2–20 mg as gargles or antimicrobials by above mentioned administration method divided in several times. The polypeptides of the present invention can be orally administered at daily doses of 2–200 mg in several portions.

The present invention will be practically explained by the following examples.

EXAMPLE 1

(1) Preparation of small granule fraction of hemocytes of horseshoe crab.

In 100 ml of hemocyte of *Tachypaeis tridentatus*, 100 ml of 3% NaCl aqua containing 0.002M propranolol was added and allowed to stand for 15 min. under conditions of ice cooling and centrifuged at 150×g for five min. at 4° C. to precipitate hemocytes. The precipitates were suspended in 20 ml of 0.008M Tris-HCl buffer containing 0.001M propranolol, 0.001M PMSF and 0.75M sucrose, pH 7.4, gently mixed and centrifuged at 400×g for 15 min. at 4° C. The resultant supernatant was added with heparin to give 40 USP unit/ml solution, centrifuged at 400×g for 10 min. at 4°

C., 5 ml of the upper layer containing granule fraction was layered on top of 8 ml of 1.5–2.4M sucrose density gradient solution containing 0.008M Tris-HCl buffer, pH 7.4, 40 USP units/ml of heparin and 0.001M PMSF, and centrifuged at 112,000×g for 30 min. at 4° C. to give two layers. The lower layer containing small granule fraction was obtained.

(2) Preparation of antimicrobial polypeptide

In 3 ml of the small granule fraction, 1 ml of a mixed solution of chloroform-methanol (1:4) was added, centrifuged to give precipitates. The precipitates were mixed with 0.05M Tris-HCl buffer containing 6M guanidine and 0.002M EDTA, pH 8.0, ultrasonicated at 10 W for 10 sec., warmed at 37° C. for 1 hr., then centrifuged. The resultant supernatant was applied to TSK gel Phenyl 5PW-RP (TOSOH Corp.) column of 4.6×75 mm previously equilibrated with 0.1 v/v % trifluoroacetic acid (TFA) and the adsorbed polypeptide was gradiently eluted with 0.1% TFA solution containing 16–48 v/v % of acetonitrile with continuous elevation of concentration, at a flow rate of 0.5 ml/min. under monitoring with UV absorption at 214 nm. The result is shown in FIG. 1. The S5 fraction shown in the FIG. 1 was applied to TSK gel ODS120T (TOSOH Corp.) column of 4.6×150 mm previously equilibrated with 0.1% TFA and the column was eluted with 0–80 v/v % of acetonitrile with continuous elevation of concentration, using a linear gradient elution at a flow rate of 0.5 ml/min. to give purified S5 fraction of polypeptide.

Figure 2:
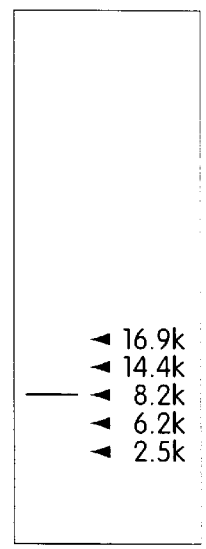
FIG. 2 shows an SDS-PAGE pattern of the polypeptide of the present invention obtained by Example 1 under reducing condition. Left pattern shows the polypeptide of the present invention and right pattern shows the marker. LMW Kit 1 (Pharmacia Biosystems Co. Ltd.) was used as the marker.

The resultant polypeptide were subjected to SDS-PAGE (sodium dodecyl sulfate-polyacrylamide gel electrophoresis) showed a single band with a calculated mass of about 8,200 under reducing condition as shown in FIG. 2.

EXAMPLE 2

(Amino acid analysis and determination of amino acid sequence)

The purified polypeptide obtained by Example 1 was applied to TSK gel Phenyl 5PW-RP (TOSOH Corp.) column of 4.6×75 mm previously equilibrated with 0.1 v/v % TFA, then said column was thoroughly washed and eluted using a linear gradient elution with acetonitrile at concentration of 8 v/v % at 10 min., 16 v/v % at 15 min., 48 v/v % at 105 min., and 80 v/v % at 110 min., at a flow rate of 0.5 ml/min. to elute the adsorbed polypeptide. During elution the concentration of polypeptide was monitored by UV absorption at 214 nm to give fractions with high concentration of the polypeptide.

The obtained polypeptide was hydrolyzed with 5.7M HCl for 24, 48 and 72 hrs. or with 4M methanesulfonic acid to determine the amino acid composition. The result is shown in Table 1. The determined amino acid composition by an amino acid analysis approximately agreed with theoretical values calculated from the amino acid sequence shown by [Formula 3] (SEQ ID NO:1).

TABLE 1

| Amino acid | Found[a] (Number of residue/ molecule) | Calculated (Number of residue/ molecule) |
|---|---|---|
| Asp | 6.0 | 6 |
| Thr | 3.2 | 3 |
| Ser | 7.0 | 7 |
| Glu | 1.3 | 1 |
| Pro | 4.0 | 3 |
| Gly | 6.1 | 6 |
| Ala | 12.0 | 12 |
| ½ Cys[b] | 4.7 | 6 |
| Val | 6.7 | 7 |
| Met | 0 | 0 |
| Ile | 3.7 | 4 |
| Leu | 3.1 | 3 |
| Tyr | 5.7 | 6 |
| Phe | 1.9 | 2 |
| Lys | 1.9 | 1 |
| His | 1.8 | 2 |
| Trp[c] | 1.8 | 2 |
| Arg | 7.5 | 8 |
| Total | | 79 |

[a]The mean values after hydrolysis with 5.7 M HCl at 110° C. for 24, 48 and 72 hrs. The values for Ser and Thr were obtained by extrapolation to 0 (zero) hr.
[b]Determination as cysteic acid given by performic acid oxidation with formic acid and hydrogen peroxide, followed by hydrolysis for 24 hrs.
[c]Determination by 4 M methanesulfonic acid method.

Determination of amino acid sequence of the resulted polypeptide by gas phase Edman degradation (Applied Biosystems Co., Ltd., Type 477A) gave the following amino acid sequence shown by [Formula 3] (SEQ ID NO:1).

```
Asn Pro Leu Ile Pro Ala Ile Tyr Ile Gly Ala Thr Val Gly Pro      [Formula 3(SEQ ID NO:1)]
 1            5                    10                    15

Ser Val Trp Ala Tyr Leu Val Ala Leu Val Gly Ala Ala Ala Val
              20                    25                    30

Thr Ala Ala Asn Ile Arg Arg Ala Ser Ser Asp Asn His Ser Cys
              35                    40                    45

Ala Gly Asn Arg Gly Trp Cys Arg Ser Lys Cys Phe Arg His Glu
              50                    55                    60

Tyr Val Asp Thr Tyr Tyr Ser Ala Val Cys Gly Arg Tyr Phe Cys
              65                    70                    75

Cys Arg Ser Arg
```

EXAMPLE 3

The apparatuses and reagents used in the below mentioned example are as follows:

Medium pressure column chromatography apparatus: Yamazen Co., Ltd., Preparative Medium Pressure Liquid Chromatograph Type YFLC-6004-FC-6R Column used for the above apparatus: SepPak C18 (Waters Ltd. (U.S.A.)), packed column Peptide Synthesizer: Applied Biosystems Co., Ltd. (U.S.A.) Type 430A Amino Acid Analyzer: Hitachi Ltd. Hitachi High Speed Amino Acid Analyzer Type L-8500

Fmoc—amino acids: Peptide Research Inst. and Watanabe Chemical Co., Ltd.

Resins for Solid Phase Synthesis: Peptide Research Inst. and Watanabe Chemical Co., Ltd.

Coupling agents: Peptide Research Inst., Watanabe Chemical Co., Ltd. and Applied Biosystems Japan Co., Ltd.

Reagents for elimination of protecting group: Peptide Research Inst. and Watanabe Chemical Co., Ltd.

Sephadex G-10 carrier: Pharmacia Biotech Co., Ltd.

Preparation of the following polypeptide [Formula 6] (SEQ ID NO:8) by solid phase synthesis.

[Chemical formula 1]

```
                    5              10              15
His-Ser-Cys-Ala-Gly-Asn-Arg-Gly-Trp-Cys-Arg-Ser-Lys-Cys-Phe-
         |_____|    ③
         |_____|              ②
                                                         ①
        20              25              30
Arg-His-Glu-Tyr-Val-Asp-Thr-Tyr-Tyr-Ser-Ala-Val-Cys-Gly-Arg-
 ②_____|

③_____     35
        Tyr-Phe-Cys-Cys-Arg-Ser-Arg-    [Formula 6]   (SEQ ID: 8)
 ①_____|
```

(wherein, His, Ser, Cys, Ala, Gly, Asn, Arg, Trp, Lys, Phe, Glu, Tyr, Val, Asp and Thr represent the before mentioned amino acid residues, and solid lines between 3rd and 34th, 10th and 28th, and 14th and 33rd represent disulfide bonds.

Nα-Fmoc group removed protected peptide—Wang resin was prepared using an Automatic Peptide Synthesizer (Peptide Synthesizer: Applied Biosystems Co., Ltd. (U.S.A.)) by a solid phase synthetic method with Fmoc strategy. Synthetic process and its control was followed by the FastMoc Program developed by Applied Biosystems Co., Ltd. (U.S.A.). This FastMoc Program adopts HBTU-HOBt method which provides rapid and highly efficient condensation reaction.

1) Starting material, Fmoc-amino acid resin: Commercial Fmoc-Arg(Pmc)-Wang resin (Watanabe Chemical Co., Ltd.) in which 37th protected Arg was introduced into hydroxymethyl-phenoxymethyl resin (Wang resin) was used.

2) Introduction of 36th Ser; Fmoc-Arg(Pmc)-Wang resin (1.25 g, 0.25 mmol; 0.2 mmol Arg/g Fmoc-Arg(Pmc)-Wang resin) and Fmoc-Ser(tBu) (383 mg, 1.00 mmol; four equivalents) were placed in a reaction vessel and Fmoc-amino acid cartridge, respectively, and were attached to the above mentioned Automatic Peptide Synthesizer and the automatic synthetic procedure of FastMoc program was performed. The operating procedure for one cycle of synthetic reaction by the program is shown below.

TABLE 2

| Operation | Reagent | Solvent | Time × repeated times |
|---|---|---|---|
| Removal of Fmoc group | 20% piperidine/ NMP | NMP | 3 min. × 1, 12 min. × 1 |
| Washing | — | NMP | 1 min. × 5 |
| Condensation reaction | Fmoc amino acid (4.0 eq) + HBTU + HOBt + DIEA* | NMP– DMF | 30 min. × 1 |
| Washing | — | NMP | 1 min. × 7 |

Required time for one cycle: 55 min.
Volume of wasted solution for one cycle: 160 ml
*Diisopropylethylamine 3) Introduction of 35th to 1st positions of amino acids;

In a similar manner as shown above, Nα-Fmoc protected Arg(Pmc), Cys(Trt), Cys(Trt), Phe, Tyr(tBu), Arg (Pmc), Gly, Cys(Trt), Val, Ala, Ser(tBu), Tyr(tBu), Tyr(tBu), Thr(tBu), Asp(OtBu), Val, Tyr(tBu), Glu (OtBu), His(Trt), Arg(Pmc), Phe, Cys(Trt), Lys(Boc), Ser(tBu), Arg(Pmc), Cys(Trt), Trp, Gly, Arg(Pmc), Asn(Trt), Gly, Ala, Cys(Trt), Ser(tBu) and His(Trt) residues were successively introduced into Wang resin according to the sequence from the C-terminal and Nα-Fmoc removed protected peptide-Wang resin (3.31 g) was obtained with almost 100% yield.

4) Preparation of peptide by deprotection of protecting group, removal of resin and partial purification;

Nα-Fmoc removed protected peptide resin prepared by the procedures of aforementioned 1) to 3) was reacted with 1M TMSOTf-thioanisole/TFA system (10 ml of TFA in the presence of m-cresol (100 eq), ethanedithiol (300 eq)) per 100 mg of the peptide resin at 25° C. for 2 hrs. The reaction mixture was filtered to remove the resin, washed twice each with 1 ml of TFA. To combined filtrate and washings, 100 ml of ice cooled and dried ether was added, and the produced precipitates was centrifuged. The residual precipitates were isolated by decantation from the supernatant, washed with cold ether and dissolved in 10 ml of 4N acetic acid (AcOH). The solution was mixed with 830 mg of dithiothreitol (80 eq) and stirred overnight at room temperature.

The reaction mixture was centrifuged and the supernatant was applied to Sephadex G-10 column of 3.7×50 cm and gel filtered with 4N AcOH. The main eluate fractions passed through the column were collected and lyophilized to give powder of partially purified un-cyclized polypeptide of [Formula 2] (SEQ ID NO:2).

5) Preparation of polypeptide [Formula 6] (SEQ ID NO:8) by air oxidation:

Aqueous solution of the partially purified un-cyclized polypeptide obtained above was adjusted to pH 7.5 with concentrated ammonia water and oxidized by aeration for cyclization. After completion of air oxidation, the reaction mixture containing oxidized cyclic polypeptide was charged to 10 g of Diaion HP-20 resin and eluted with 60% acetonitrile ($CH_3CN$) in 1N AcOH. The eluate was concentrated under reduced pressure at room temperature to remove $CH_3CN$ and pulverized by lyophilization.

The lyophilized powder was dissolved in a small amount of water and applied to SepPak medium pressure column (24×190 mm) and eluted by gradient elution with acetonitrile in 0.1% TFA aqueous solution monitoring by absorption at 280 nm for partial purification to give the desired fraction with purities of 40–50%. The desired fractions were collected, evaporated under reduced pressure, lyophilized to give a powder. The powder product was dissolved in a small amount of water and applied to Asahi Pack ODP-90 column (2.15×30 cm) (Asahi Chemical Industry Co., Ltd.) attached to the following HPLC system. The column was eluted by gradient elution with $CH_3CN$ and purified by the HPLC (TOSOH Corp., Full Automatic HPLC, Type HLC-8070) to give a single peak of the desired peptide [Formula 6] (SEQ ID NO:8) in a yield of 13% calculated based on protecting group-protected peptide resin.

6) Analysis of polypeptide;

The purified polypeptide by the above process 5), was subjected to acid hydrolysis with 4M methanesulfonic acid containing 0.2% tryptamine at 115° C. for 24 hrs. according to the method of Liu et al. (Liu, T. Y. et al., J. Biol. Chem., 251, 1936 (1976) to determine the amino acid composition. The composition was satisfactorily agreed with that of calculated from amino acid sequence of aforementioned [Formula 6] (SEQ ID NO:8).

An analytical reversed phase HPLC profile of polypeptide (Shimadzu Co., Ltd., HPLC Type LC-6AD; TSK ODS-120T (TOSOH Corp., 0.46×15 cm) column and TSK ODS-120T guard column (0.32×1.5 cm)) showed single peak at 22.8 min.

Control samples of antimicrobial peptide tachyplesinI (Nakamura, H. et al., J. Biol. Chem., 263, 16709 (1988)) and anti-HIV active peptide T22 (Nakashima, H. et al. Antimicrobial Agents and Chemotherapy, 36, 1249 (1992)) on the above analytical reverse phase HPLC showed elution time of 24.1 and 17.2 min., respectively.

The conditions of the analytical reversed phase HPLC are as follows: two gradient eluting solutions of 0.1% TFA aqueous solution containing 10% $CH_3CN$ (A solution) and 0.1% TFA aqueous solution containing 80% $CH_3CN$ (B solution); gradient elution with mixtures of 0% of B solution at one min. and 42% of B solution at 29.4 min. at column temperature of 40° C.; flow rate of 0.8 ml/min.; detection wave length of 220 and 280 nm, and sample injection volume of 20 μl at a peptide concentration of 0.1 mg/ml.

EXAMPLE 4

(Determination of antimicrobial activity)

Various microorganisms shown in Table 3 were suspended in 10 mM phosphate buffer, pH 7.0 (hypotonic solution). In 900 μl of 5,000–10,000 CFU/ml suspension, 100 μl of 2-fold serial diluted polypeptide solution at a concentration of 20 μg/ml obtained by Example 1 was added and incubated at 37° C. for 1 hr. Then, 100 μl of incubated mixture was inoculated in an agar medium, cultured at 37° C. for 12 hrs. and the number of colonies was counted with naked eye (see Infections and Immunity, 42, 10–14 (1983)). CFU means colony forming unit.

The results are shown in Table 3. As clearly shown in Table 3, the polypeptide of the present invention exhibited potent antimicrobial activity against Gram negative and positive bacteria, and fungi.

TABLE 3

| Microorganisms | $IC_{50}$ (μg/ml) (hypotension) |
|---|---|
| Gram negative bacteria | |
| *Escherichia coli* | 2.5 |
| *Salmonella typhimurium* LT2(S) | 20 |
| *S. minnesota* Re | <0.6 |

TABLE 3-continued

| Microorganisms | $IC_{50}$ (μg/ml) (hypotension) |
|---|---|
| *Klebsiella pneumoniae* Gram positive bacterium | <1.3 |
| *Staphylococcus aureus* Fungus | <2.5 |
| *Candida albicans* | 10–20 |

EXAMPLE 5

In 50 mM Tris-HCl buffer, pH 8, two mg of purified polypeptide obtained by Example 1 and 20 μg of trypsin (Sigma Co., Ltd.) were added and incubated at 37° C. for 24 hrs. to degrade and to give polypeptide fractions. The degraded mixture was applied to YMC-Pack 5C4 (YMC Co., Ltd.) column (4.6×150 mm) previously equilibrated with 0.06 v/v % TFA and eluted with 0.052% TFA solution containing gradiently elevated 0–80 v/v % $CH_3CN$ at 5–55 min. at a flow rate of 0.5 ml/min. to give polypeptide fractions. The eluate was monitored with UV absorption rate at 210 nm and fractions with high peptide concentration were collected at 27 and 47.6 min. to give two polypeptide fractions. The resultant fractions were referred as T3 and T6 polypeptide fraction, respectively.

The two polypeptide fractions were hydrolyzed with 5.7M HCl at 110° C. for 24 hrs. and the amino acid composition was determined. The results are shown in Table 4. The determined amino acid compositions of polypeptide fractions T3 and T6 were approximately agreed with theoretical compositions calculated from [Formula 4] (SEQ ID NO:3) and [Formula 5] (SEQ ID NO:4).

TABLE 4

| | Polypeptide | | | |
|---|---|---|---|---|
| | Fraction T3 | | Fraction T6 | |
| Amino acid | Anal. (residue No./molecule) | Calcd. | Anal. (residue No./molecule) | Calcd. |
| Asp | 4.0 | (4) | 1.9 | (2) |
| Thr | 1.1 | (1) | 2.3 | (2) |
| Ser | 5.0 | (6) | 1.2 | (1) |
| Glu | 1.2 | (1) | — | — |
| Pro | — | — | 2.8 | (3) |
| Gly | 3.4 | (3) | 3.3 | (3) |
| Ala | 3.4 | (3) | 9.5 | (9) |
| ½ Cys | N.D. | (6) | N.D. | (0) |
| Val | 2.1 | (2) | 5.2 | (5) |
| Met | — | — | — | — |
| Ile | — | — | 3.8 | (4) |
| Leu | — | — | 3.0 | (3) |
| Tyr | 4.0 | (4) | 2.1 | (2) |
| Phe | 1.5 | (2) | — | — |
| Lys | 1.0 | (1) | — | — |
| His | 2.0 | (2) | — | — |
| Trp | N.D. | (1) | N.D. | (1) |
| Arg | 6.7 | (6) | 1.6 | (2) |
| Total | | (42) | | (37) |

EXAMPLE 6

(Antimicrobial activity)

*Escherichia coli* was suspended in 10 mM phosphate buffer, pH 7.0, at a concentration of 10,000 CFU/ml and 450 μl of the suspension was mixed with 50 μl each of polypeptide fraction T3 (polypeptide of [Formula 4]) (SEQ ID NO:3), T6 (polypeptide of [Formula 5]) (SEQ ID NO:4), and a polypeptide obtained by Example 1 each having a concentration of 40 μg/ml, and as a control 10 mM phosphate buffer, pH 7.0. The mixtures were incubated at 37° C. for 1 hr. Then, 100 μl of incubated mixture was inoculated in an agar medium, cultured at 37° C. for 12 hrs. and the number of colonies were counted with naked eye. Polypeptide fractions T3 (polypeptide of [Formula 4]) (SEQ ID NO:3) and T6 (polypeptide of [Formula 5]) (SEQ ID NO:4), and a polypeptide obtained by Example 1 inhibited the growth of *Escherichia coli* at a rate of about 90%, about 20% and about 95% or over, respectively.

In addition, *Staphylococcsii aureus* was suspended in 10 mM phosphate buffer, pH 7.0, at a concentration of 5,000 CFU/ml and 450 μl of the suspension was mixed with 50 μl each of polypeptide fraction T3 (polypeptide of [Formula 4]), T6 (polypeptide of [Formula 5]) (SEQ ID NO:4), and a polypeptide obtained by Example 1 each having a concentration of 40 μg/ml, and as a control 10 mM phosphate buffer, pH 7.0. The mixtures were incubated at 37° C. for 1 hr. Then, 100 μl of incubated mixture was inoculated in an agar medium, cultured at 37° C. for 12 hrs. and the number of colonies were counted with naked eye. Polypeptide fraction T3 (polypeptide of [Formula 4]) (SEQ ID NO:3) and T6 (polypeptide of [Formula 5]) (SEQ ID NO:4), and a polypeptide obtained by Example 1 inhibited the growth of *Staphylococcus aureus* at a rate of about 30%, about 70% and almost completely, respectively.

As clearly shown by these results, the polypeptide fractions of the present invention exhibited potent antimicrobial activity against Gram negative and positive bacteria, particularly, polypeptide fraction T3 (polypeptide of [Formula 4]) (SEQ ID NO:3) and T6 (polypeptide of [Formula 5]) (SEQ ID NO:4) exhibited potent antibacterial activity against Gram negative bacteria *Escherichia coli* and Gram positive bacteria *Staphylococcuis aureus*, respectively.

EXAMPLE 7
[Preparation of DNA encoding for polypeptides]
1. Synthesis of an oligonucleotide His-Glu-Tyr-Val-Asp-Thr, amino acid Nos. 59–64) of SEQ ID NO:1 in the amino acid sequence determined by Example 2 was reverse translated as an antisense. A mixture of oligonucleotides composed of 25 base pairs having the recognition sequence of restriction enzyme (EcoRI) and two bases for the protection of DNA at 5'-terminal was synthesized using DNA synthesizer 380A (Applied Biosystems Japan Co., Ltd.).

3'-GTACTTATACATCTATGCTTAAGGA-5' [Formula 7] (SEQ ID NO:9)
```
    G  C  G  C  G
          A
          G
```

The oligonucleotide shown here includes all possibilities of the complementary sequence to a nucleotide sequence which was reverse translated from His-Glu-Tyr-Val-Asp-Thr amino acid Nos. 59–64 of SEQ ID NO:1), (however, a 5'-terminal nucleotide (T/G/C/A) of a complementary nucleotide sequence (3'-TG(T/G/C/A)-5') in codon of Thr was excluded.

2. Preparation of poly(A)+RNA containing mRNA encoding for polypeptide.

Poly(A)+RNA was isolated from hemocytes of horseshoe crab, since the polypeptide of the present invention is obtained and purified from hemocytes of horseshoe crab.

(1) Preparation of total RNA

By using of AGPC method (see Experimental Medicine (Jikken Igaku) 9, 1937–1940 (1991), Pub. by Yodosha Co., Ltd.), about 11 mg of total RNA was isolated from 11.8 g of limulus hemocytes.

(2) Preparation of poly(A)+RNA

Poly(A)+RNA was isolated from about 2 mg of the above mentioned total RNA with Oligotex-dT 30 Super kit (Nippon Roche K.K.). The similar procedure was repeated once again for further purification to obtain 34.5 μg of highly purified poly(A)+RNA from 2 mg of total RNA.

3. Preparation of cDNA library of hemocytes of horseshoe crab.

(1) Synthesis of cDNA cDNA was synthesized from poly(A)+RNA obtained in the above mentioned process 2. using Superscript™ Choice System (Gibco BRL Co., Ltd.).

(2) Preparation of cDNA library

λZIPLOX horseshoe crab hemocyte cDNA library was prepared from cDNA prepared in the above mentioned process 3. (1) using λZIPLOX, EcoRI Arms™ (Gibco BRL Co., Ltd.) and λPackaging System™.

4. CDNA cloning of polypeptide.

A DNA fragment encoding for a part of polypeptide of [Formula 3] was amplified using phage DNA prepared from λgt10 cDNA library prepared by Seki, N., et al. (J. Biol. Chem., 269, 1370–1374 (1994)) as a template and two oligonucleotides as primers, that is the oligonucleotide synthesized in the above process 1, and a synthetic oligonucleotide having the same 3'-ATGGGACCTTCTTTATGAGTAT-5' (SEQ ID NO:10) sequence with that of around EcoRI restriction enzyme recognition sequence of phage vector λgt10 by PCR method (Saiki, R. K., et al. Science, 239, 487–491 (1988)). The DNA fragment was labeled with [α-$^{32}$P]dCTP using Ready-to-Go™ DNA labeling kit (Pharmacia Biotech Co., Ltd.) to obtain a DNA probe. The probe was used for screening of the λZIPLOX cDNA library prepared in the above mentioned 3.(2) to obtain a positive clone containing a longest insert cDNA having 581 bp. The nucleotide sequence of the insert cDNA was analyzed.

5. Determination of cDNA nucleotide sequence encoding for the polypeptide.

The positive clone obtained by the above mentioned process 4. was transfected to attached *E.coli* DH10B(ZIP) according to the direction in the package insert of λZIPLOX, EcoRI Arm™ to give a plasmid containing cDNA encoding for said polypeptide. A subcloning with deletion using a restriction enzyme recognition site on cDNA fragment and Kilo-sequence deletion kit (Takara Shuzo Co., Ltd.) was performed to determine the total nucleotide sequence of the insert cDNA. The nucleotide sequence of cDNA of clone prepared by the above mentioned procedure was determined using DNA sequencer 373A (Applied Biosystems Japan Co., Ltd. (ABI Co., Ltd.)). In the process, a universal primer (ABI Cc., Ltd.), synthetic oligonucleotides (5'-TGTAAAACGACGGCCAGT-3' (SEQ ID NO:11), 5'-CAGGAAACAGCTATGACC-3') (SEQ ID NO:12) mimicked the nucleotide sequence of M13 reverse primer and a synthetic oligonucleotide (5'-CGAGCCTCTTCTGATAAC-3') (SEQ ID NO:1) prepared by reverse translation of Arg-Ala-Ser-Ser-Asp-Asn amino acid Nos. 37–42 of SEQ ID NO:1) sequence in the amino acid sequence of polypeptide of [Formula 3] (SEQ ID NO:1) were used as sequencing primers, since plasmid containing insert cDNA obtained from positive clone was M13 plasmid.

The determined nucleotide sequence of cDNA of said polypeptide and the deduced amino acid sequence are shown in (SEQ ID NO:5). The determined amino acid sequence includes the all of amino acid sequence SEQ ID NO:1 determined by Example 2, and the insert cDNA whose nucleotide sequence was determined by the procedure, was confirmed its encoding of said polypeptide.

EXAMPLE 8

(Preparation of pharmaceutical composition)

(1) External preparation for wound healing:

1 g cream

| | |
|---|---|
| Polypeptide obtained by Example 1 | 10 mg |
| Sorbitan monostearate | 7 mg |
| Polyoxyethylene sorbitan monostearate | 7 mg |
| Isopropyl palmitate | 37 mg |
| Vaseline | 37 mg |
| Liquid paraffin | 37 mg |
| Cetanol | 50 mg |
| Glycerin | 70 mg |
| Magnesium stearate | 2 mg |
| were added to purified water to make 1 g cream | |
| (2) Oral preparation | |
| A polypeptide fraction of Example 5 | 100 mg |
| Lactose | 80 mg |
| Total | 180 mg |

Above components were homogeneously mixed and filled in a hard capsule to give a capsule preparation.

We claim:

1. A single stranded DNA comprising a nucleotide sequence encoding the polypeptide shown by Formula 3 (SEQ ID NO:1):

```
                        (Formula 3(SEQ ID NO:1))
Asn Pro Leu Ile Pro Ala Ile Tyr Ile Gly Ala Thr Val
 1               5                  10
Gly Pro Ser Val Trp Ala Tyr Leu Val Ala Leu Val Gly
         15              20              25
Ala Ala Ala Val Thr Ala Ala Asn Ile Arg Arg Ala Ser
                 30                  35
Ser Asp Asn His Ser Cys Ala Gly Asn Arg Gly Trp Cys
40                   45                  50
Arg Ser Lys Cys Phe Arg His Glu Tyr Val Asp Thr Tyr
         55                  60              65
Tyr Ser Ala Val Cys Gly Arg Tyr Phe Cys Cys Arg Ser
                 70                  75
Arg
``` wherein, cysteine residues at 45th, 52nd, 56th, 70th, 75th and 76th positions may form disulfide bond (—S—S—) between at least one combination of 45th and 76th, 52nd and 70th, and 56th and 75th positions.

2. The DNA according to claim 1 consisting of nucleotides sequence Nos. 135–371 of SEQ ID NO:5.

3. The double stranded DNA comprising the DNA according to claim 1 or 2 and a DNA complementary with said DNA.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 79 amino acids
        (B) TYPE: amino acid
        (C) STRANDEDNESS: single
        (D) TOPOLOGY: linear (ix) FEATURE:
        (A) NAME/KEY: Peptide
        (B) LOCATION: 1..79
        (D) OTHER INFORMATION: /label= FORMULA 3

(xi) SEQUENCE DESCRIPTION: SEQ ID NO:1:

Asn Pro Leu Ile Pro Ala Ile Tyr Ile Gly Ala Thr Val Gly Pro Ser
1               5                   10                  15

Val Trp Ala Tyr Leu Val Ala Leu Val Gly Ala Ala Val Thr Ala
            20                  25                  30

Ala Asn Ile Arg Arg Ala Ser Ser Asp Asn His Ser Cys Ala Gly Asn
            35                  40                  45

Arg Gly Trp Cys Arg Ser Lys Cys Phe Arg His Glu Tyr Val Asp Thr
    50                  55                  60

Tyr Tyr Ser Ala Val Cys Gly Arg Tyr Phe Cys Cys Arg Ser Arg
65                  70                  75

(2) INFORMATION FOR SEQ ID NO:2:

(i) SEQUENCE CHARACTERISTICS:
        (A) LENGTH: 37 amino acids
        (B) TYPE: amino acid
        (C) STRANDEDNESS: single
        (D) TOPOLOGY: linear (ix) FEATURE:

```
    (A) NAME/KEY: Peptide
    (B) LOCATION: 1..7
    (D) OTHER INFORMATION: /label= FORMULA 2

(xi) SEQUENCE DESCRIPTION: SEQ ID NO:2:

His Ser Cys Ala Gly Asn Arg Gly Trp Cys Arg Ser Lys Cys Phe Arg
1               5                   10                  15

His Glu Tyr Val Asp Thr Tyr Tyr Ser Ala Val Cys Gly Arg Tyr Phe
            20                  25                  30

Cys Cys Arg Ser Arg
        35

(2) INFORMATION FOR SEQ ID NO:3:

(i) SEQUENCE CHARACTERISTICS:
        (A) LENGTH: 42 amino acids
        (B) TYPE: amino acid
        (C) STRANDEDNESS: single
        (D) TOPOLOGY: linear (ix) FEATURE:
        (A) NAME/KEY: Peptide
        (B) LOCATION: 1..42
        (D) OTHER INFORMATION: /label= FORMULA 4

(xi) SEQUENCE DESCRIPTION: SEQ ID NO:3:

Ala Ser Ser Asp Asn His Ser Cys Ala Gly Asn Arg Gly Trp Cys Arg
1               5                   10                  15

Ser Lys Cys Phe Arg His Glu Tyr Val Asp Thr Tyr Tyr Ser Ala Val
            20                  25                  30

Cys Gly Arg Tyr Phe Cys Cys Arg Ser Arg
        35                  40

(2) INFORMATION FOR SEQ ID NO:4:

(i) SEQUENCE CHARACTERISTICS:
        (A) LENGTH: 36 amino acids
        (B) TYPE: amino acid
        (C) STRANDEDNESS: single
        (D) TOPOLOGY: linear (ix) FEATURE:
        (A) NAME/KEY: Peptide
        (B) LOCATION: 1..36
        (D) OTHER INFORMATION: /label= FORMULA 5

(xi) SEQUENCE DESCRIPTION: SEQ ID NO:4:

Asn Pro Leu Ile Pro Ala Ile Tyr Ile Gly Ala Thr Val Gly Pro Ser
1               5                   10                  15

Val Trp Ala Tyr Leu Val Ala Leu Val Gly Ala Ala Ala Val Thr Ala
            20                  25                  30

Ala Asn Ile Arg
        35

(2) INFORMATION FOR SEQ ID NO:5:

(i) SEQUENCE CHARACTERISTICS:
        (A) LENGTH: 581 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 21..371

(xi) SEQUENCE DESCRIPTION: SEQ ID NO:5:
```

```
GATTGGTATC AACAAACACA ATG AAA GGA AAC ATC GGT ATT GCT GTG TTC              50
                     Met Lys Gly Asn Ile Gly Ile Ala Val Phe
                      1               5                  10

TAC ATG TTG TTA CTT CTA CTT CCA ACA GAC AGT ATT GGG AAG AAG ATG            98
Tyr Met Leu Leu Leu Leu Leu Pro Thr Asp Ser Ile Gly Lys Lys Met
                 15                  20                  25

GAA GAA GAG CAA GAG AAA CTT TTC AGA CAA AAA CGA AAT CCT CTC ATT           146
Glu Glu Glu Gln Glu Lys Leu Phe Arg Gln Lys Arg Asn Pro Leu Ile
                 30                  35                  40

CCA GCA ATT TAC ATT GGA GCA ACT GTT GGG CCT TCA GTT TGG GCT TAT           194
Pro Ala Ile Tyr Ile Gly Ala Thr Val Gly Pro Ser Val Trp Ala Tyr
             45                  50                  55

CTG GTC GCT TTA GTT GGT GCC GCT GCC GTT ACT GCT GCA AAT ATA AGA           242
Leu Val Ala Leu Val Gly Ala Ala Ala Val Thr Ala Ala Asn Ile Arg
         60                  65                  70

CGA GCC TCT TCT GAT AAC CAT TCC TGT GCT GGC AAC AGA GGT TGG TGT           290
Arg Ala Ser Ser Asp Asn His Ser Cys Ala Gly Asn Arg Gly Trp Cys
75                  80                  85                  90

AGG TCA AAG TGT TTC CGT CAC GAA TAT GTG GAC ACT TAC TAC AGT GCT           338
Arg Ser Lys Cys Phe Arg His Glu Tyr Val Asp Thr Tyr Tyr Ser Ala
                 95                 100                 105

GTA TGT GGA AGA TAC TTT TGC TGC AGA TCA CGC TAACAGATGG CACTCTGACA         391
Val Cys Gly Arg Tyr Phe Cys Cys Arg Ser Arg
             110                 115

AAGTATCTGA ATTTGAGGTG TAACCAAGAA AACTAAAGCC ATATTAAGTA AACAGTTCTA         451

AACATTTCAA GGTATTTAGA GTAATTTAGT AATGTCTAGA TAGTATTATG TCTTCTTACC         511

AATATATATA TTCGTAGTGT ATGAGTATGT TTTACGTTAT CTGACAGTCA ATAAATATGT         571

TTCTATCAAT                                                                581
```

(2) INFORMATION FOR SEQ ID NO:6:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:6:

```
Met Lys Gly Asn Ile Gly Ile Ala Val Phe Tyr Met Leu Leu Leu
 1               5                  10                  15

Leu Pro Thr Asp Ser Ile Gly Lys Lys Met Glu Glu Glu Gln Glu Lys
             20                  25                  30

Leu Phe Arg Gln Lys Arg Asn Pro Leu Ile Pro Ala Ile Tyr Ile Gly
         35                  40                  45

Ala Thr Val Gly Pro Ser Val Trp Ala Tyr Leu Val Ala Leu Val Gly
     50                  55                  60

Ala Ala Ala Val Thr Ala Ala Asn Ile Arg Arg Ala Ser Ser Asp Asn
 65                  70                  75                  80

His Ser Cys Ala Gly Asn Arg Gly Trp Cys Arg Ser Lys Cys Phe Arg
                 85                  90                  95

His Glu Tyr Val Asp Thr Tyr Tyr Ser Ala Val Cys Gly Arg Tyr Phe
                100                 105                 110

Cys Cys Arg Ser Arg
             115
```

(2) INFORMATION FOR SEQ ID NO:7:

(i) SEQUENCE CHARACTERISTICS:

(A) LENGTH: 37 amino acids
                    (B) TYPE: amino acid
                    (C) STRANDEDNESS: single
                    (D) TOPOLOGY: linear (ix) FEATURE:
                    (A) NAME/KEY: Peptide
                    (B) LOCATION: 1..37
                    (D) OTHER INFORMATION: /label= FORMULA 1/note= "wherein each
                        Xaa is independently selected from a group of one or
                        more specified amino-acids as defined in the
                        specification"

(xi) SEQUENCE DESCRIPTION: SEQ ID NO:7:

Xaa Xaa Cys Xaa Xaa Xaa Xaa Xaa Xaa Cys Arg Ser Xaa Cys Phe Arg
1               5                   10                  15

Xaa Glu Xaa Xaa Xaa Xaa Xaa Xaa Ser Ala Xaa Cys Gly Arg Tyr Xaa
            20                  25                  30

Cys Cys Arg Xaa Xaa
            35

(2) INFORMATION FOR SEQ ID NO:8:

(i) SEQUENCE CHARACTERISTICS:
                    (A) LENGTH: 37 amino acids
                    (B) TYPE: amino acid
                    (C) STRANDEDNESS: single
                    (D) TOPOLOGY: linear (ix) FEATURE:
                    (A) NAME/KEY: Peptide
                    (B) LOCATION: 1..37
                    (D) OTHER INFORMATION: /label= FORMULA 6

(xi) SEQUENCE DESCRIPTION: SEQ ID NO:8:

His Ser Cys Ala Gly Asn Arg Gly Trp Cys Arg Ser Lys Cys Phe Arg
1               5                   10                  15

His Glu Tyr Val Asp Thr Tyr Tyr Ser Ala Val Cys Gly Arg Tyr Phe
            20                  25                  30

Cys Cys Arg Ser Arg
            35

(2) INFORMATION FOR SEQ ID NO:9:

(i) SEQUENCE CHARACTERISTICS:
                    (A) LENGTH: 25 base pairs
                    (B) TYPE: nucleic acid
                    (C) STRANDEDNESS: single
                    (D) TOPOLOGY: linear (xi) SEQUENCE DESCRIPTION: SEQ ID NO:9:

AGGAATTCGT RTCNACRTAY TCRTG                                                25

(2) INFORMATION FOR SEQ ID NO:10:

(i) SEQUENCE CHARACTERISTICS:
                    (A) LENGTH: 22 base pairs
                    (B) TYPE: nucleic acid
                    (C) STRANDEDNESS: single
                    (D) TOPOLOGY: linear (xi) SEQUENCE DESCRIPTION: SEQ ID NO:10:

TATGAGTATT TCTTCCAGGG TA                                                   22

(2) INFORMATION FOR SEQ ID NO:11:

(i) SEQUENCE CHARACTERISTICS:
                    (A) LENGTH: 18 base pairs (B) TYPE: nucleic acid
(C) STRANDEDNESS: single
(D) TOPOLOGY: linear (xi) SEQUENCE DESCRIPTION: SEQ ID NO:11:

TGTAAAACGA CGGCCAGT                                    18

(2) INFORMATION FOR SEQ ID NO:12:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:12:

CAGGAAACAG CTATGACC                                    18

(2) INFORMATION FOR SEQ ID NO:13:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:13:

CGAGCCTCTT CTGATAAC                                    18